United States Patent [19]  
Paul

[11] 4,218,468  
[45] Aug. 19, 1980

[54] KETONE INSECTICIDES  
[75] Inventor: Jill H. Paul, Edgewater, N.J.  
[73] Assignee: Mobil Oil Corporation, New York, N.Y.  
[21] Appl. No.: 959,820  
[22] Filed: Nov. 13, 1978  
[51] Int. Cl.² .................. A01N 9/20; A01N 9/24; C07C 121/76; C07C 49/84  
[52] U.S. Cl. ............... 424/282; 260/340.5 R; 260/347.8; 260/465 R; 260/465 F; 260/465 G; 260/465 K; 568/325; 568/43; 424/285; 424/304; 424/331; 260/347.2; 260/455 R; 424/301; 568/329; 568/306; 568/313; 568/315; 568/31  
[58] Field of Search ........... 260/465 F, 590 C, 590 D, 260/340.5 R, 465 G, 455 R, 347.2; 424/331, 282, 304, 301

[56] References Cited  
U.S. PATENT DOCUMENTS  
3,987,102 10/1976 Karrer .................. 260/465 F  
4,062,968 12/1977 Fujimoto et al. .......... 260/465 D  
4,065,508 12/1977 Karrer .................. 424/331

Primary Examiner—Dolph H. Torrence  
Attorney, Agent, or Firm—Charles A. Huggett; James F. Powers, Jr.; Hastings S. Trigg

[57] ABSTRACT

There are provided insecticidal ketones having the general structure:

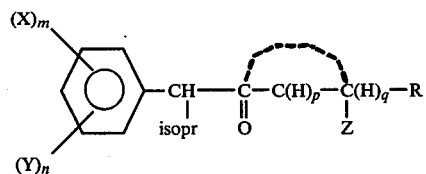

insecticidal compositions containing the ketones and a carrier, and the method of controlling insects with the ketones.

15 Claims, No Drawings

KETONE INSECTICIDES

BACKGROUND OF THE INVENTION

1. Field of the Invention

This invention is concerned with certain ketones that have insecticidal activity.

2. Description of the Prior Art

The insecticides of this invention have a similarity in structure to esters described in U.S. Pat. No. 4,062,968. Insofar as is now known, the ketones described herein have not been proposed.

SUMMARY OF THE INVENTION

This invention provides compounds having the formula:

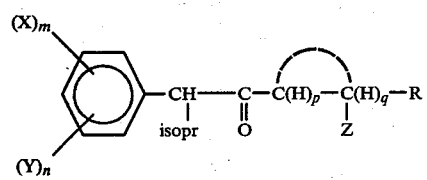

wherein isopr is isopropyl; X and Y are halogen, cyano, nitro, $C_1$-$C_4$ alkyl, $C_1$-$C_4$ alkenyl, propargyl, $C_1$-$C_4$ alkoxy, phenoxy, $C_1$-$C_4$ haloalkyl, $C_1$-$C_4$ alkylthio, or $C_1$-$C_4$ alkylsulfonyl or X and Y combined are methylenedioxy; m is 1-5; n is 0-5; p is 1 or 2 and q is 0 or 1 and when p is 1 and q is 0, the symbol ⌒ is a bond forming part of a double bond or a methylene group forming a cyclopropy ring; Z is hydrogen or cyano; and R is

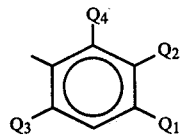

wherein $Q_2$ is phenyl, phenoxy, benzyl, propargyl, thiophenoxy, furfuryl, halogen, alkyl, hydrogen, or trifluoromethyl; $Q_1$ is hydrogen, chlorine, phenoxy, benzyl or thiophenoxy or $Q_1$ and $Q_2$ together can be cyclopentyl or cyclohexyl; $Q_3$ is hydrogen, methyl or chlorine; and $Q_4$ is hydrogen or methyl.

DESCRIPTION OF SPECIFIC EMBODIMENTS

In general, the insecticidal ketones of this invention are prepared:

General Scheme for Synthesis of Insecticidal Ketones

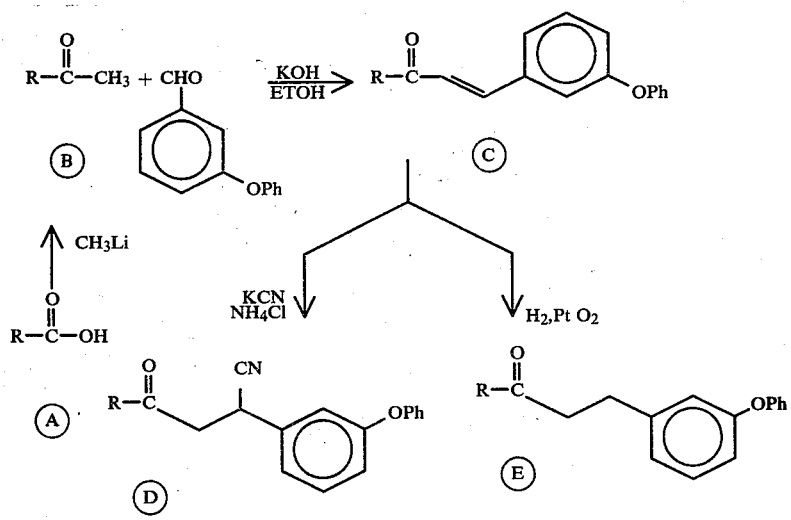

The preparation of starting carboxylic acid (A) is described in U.S. Pat. No. 4,062,968, particularly in Columns 105-110, which is incorporated herein by reference.

General Procedure for Methyl Ketones ((B))

To a solution of 0.047 mole of the appropriate carboxylic acid in 300 ml. of dry ether, is added dropwise 0.142 mole of $CH_3Li$, while maintaining the reaction temperature at 0° C. by means of an ice-salt bath. The reaction mixture is allowed to warm to R.T. and stir overnight. The whole is poured into 80 ml. of conc. HCl over 800 ml. of ice. The layers are separated and the aqueous layer is extracted 2× with ether. The combined organic extracts are washed 1× with 10% $Na_2CO_3$, 1× with $H_2O$, dried over $MgSO_4$, and concentrated under reduced pressure to yield 0.038 mole of product.

IR ($cm^{-1}$) 1709 (s).

General Procedure for α,B - Unsaturated Ketone ( © )

A mixture of 0.0095 mole of methyl ketone, 0.0136 mole of m-phenoxy benzaldehyde or other substituted benzaldahyde and 0.0025 mole of KOH in 70 ml. of EtOH is heated to 60° C., by means of a temperature control device for 16 hrs. Upon cooling, the whole is poured into 200 ml. of $H_2O$. The resulting oil is extracted into ether (2×). The ether extracts are washed with $H_2O$ and concentrated under reduced pressure. The residue is stirred with saturated $NaHSO_3$ for 1 hr. to remove the excess aldehyde. The bisulfite addition product is filtered off after dilution with ether. The ether layer of the filtrate is dried over $MgSO_4$ and concentrated under reduced pressure to yield 0.0064 mole of product.

IR ($cm^{-1}$) 1695(s), 1666(s), 980(br,s).

General Procedure for β-Cyano Ketones ((D))

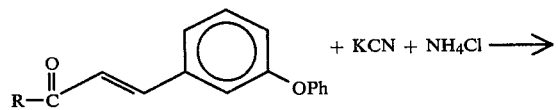

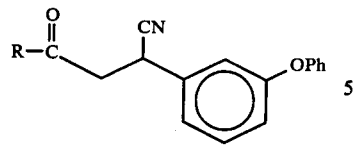

To a solution of 0.03 mole of the α,β unsaturated ketone dissolved in 120 ml. of DMF is added 0.06 mole of KCN in 25 ml. of H₂O, causing a slight exotherm. To this mixture is added 0.045 mole of ammonium chloride. The reaction mixture is heated to 98° C. for 5 hrs. The whole is poured into H₂O and the resulting oil taken up in ether. The ether extract is washed 3× with H₂O, dried, and concentrated under reduced pressure to yield 0.028 mole of product.

IR (cm$^{-1}$) 2272(s), 2222(s), 1724(brS).

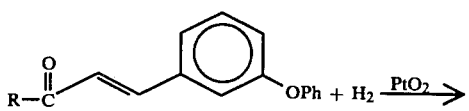

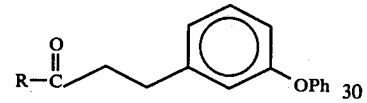

A solution of 0.03 mole of the α,β unsaturated ketone dissolved in 100 ml. of EtOAc and 100 mg. of PtO₂ is placed in a dry Parr Shaker hydrogenation bottle. H₂ is introduced overnight. The catalyst is filtered and washed with EtOAc. The filtrate is concentrated under reduced pressure to yield 0.03 mole of product.

IR (cm$^{-1}$) 1709(s).

Non-limiting examples of the ketones of this invention are:

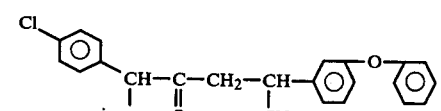
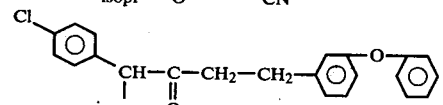
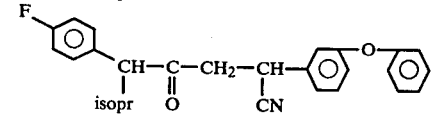
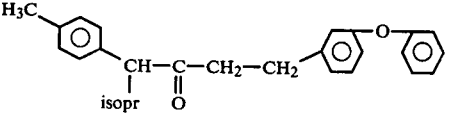
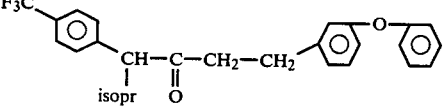
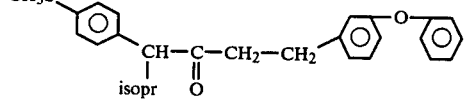

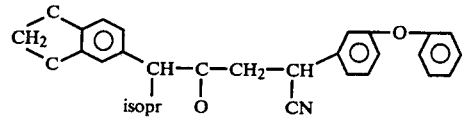
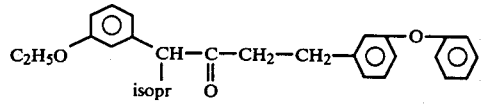
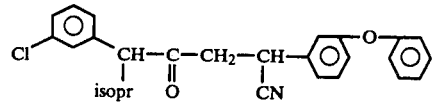
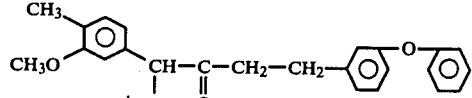
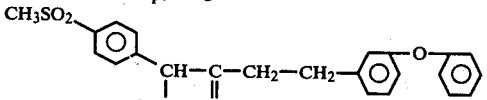
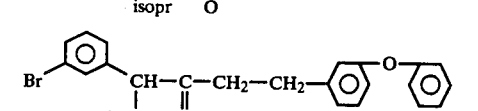
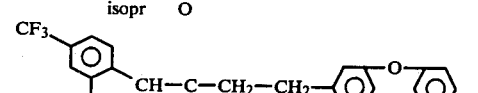
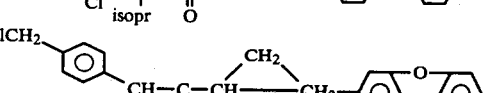
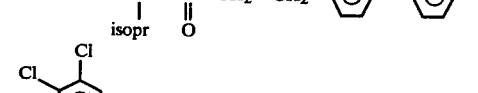
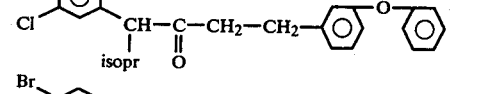
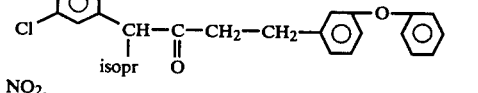
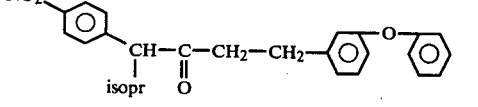

-continued

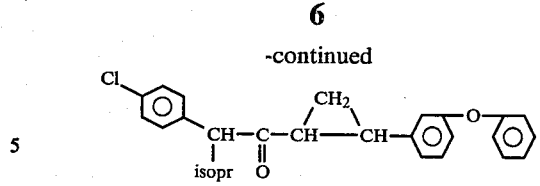

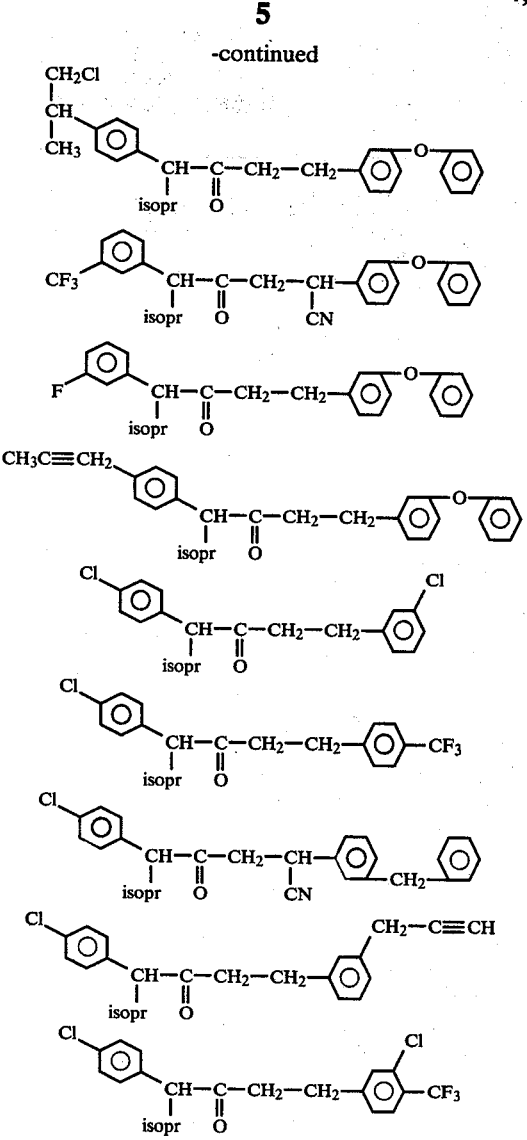

The following examples demonstrate compounds of this invention prepared by the aforedescribed general procedures.

EXAMPLE 1

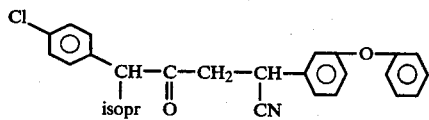

EXAMPLE 2

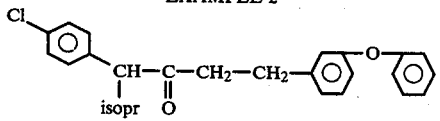

EXAMPLE 3

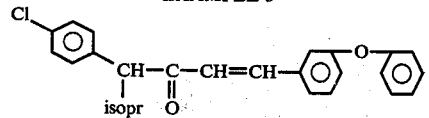

EXAMPLE 4

The compounds of this invention have been found to exhibit considerable biological activity. They are especially potent pesticides when used to control or combat important agricultural pests. These compounds can be used in various ways to achieve biological action. They can be applied per se, solids or in vaporized form, but are preferably applied as the toxic components in pesticidal compositions of the compound and a carrier. The compositions can be applied as dusts, as liquid sprays, or as gas-propelled sprays and can contain, in addition to a carrier, additives such as emulsifying agents, wetting agents, binding agents, gases compressed to the liquid state, odorants, stabilizers and the like. A wide variety of liquid and solid carriers can be used in the pesticidal compositions. Non-limiting examples of liquid carriers include water; organic solvents such as alcohols, ketones, amides, and esters; mineral oils such as kerosene, light oils, and medium oils, and vegetable oils such as cottonseed oil. Non-limiting examples of solid carriers include talc, bentonite, diatomaceous earth, pyrophylite, fullers earth, gypsum, flours derived from cotton seeds and nut shells, and various natural and synthetic clays having a pH not exceeding about 9.5.

The amount of the compounds of this invention utilized in pesticidal compositions will vary rather widely. It depends to some extent upon the type of composition in which the material is being used, the nature of the condition to be controlled, and the method of application (i.e., spraying dusting etc.). In the ultimate pesticidal composition, as applied in the field, pesticide concentrations as low as 0.0001 weight percent of the total composition can be used. In general, compositions, as applied, containing about 0.05 weight percent pesticide in either liquid or solid carrier give excellent results. In some cases, however, stronger dosages up to about 10 weight percent may be required.

In practice, pesticidal compositions are usually prepared in the form of concentrates, which are diluted in the field to the concentration desired for application. For example, the concentrate can be a wettable powder containing large amounts of the compound of this invention, a carrier (e.g. attapulgite or other clay), and wetting and dispersing agents. Such powders can be diluted prior to application, by dispersing it in water to obtain a sprayable suspension containg the concentration of pesticide desired for application. Other concentrates can be solutions that can be later diluted, e.g. with kerosene. Thus, it is within the contemplation of this invention to provide pesticidal compositions containing up to about 80 percent, by weight of the composition, of a pesticidal compound of this invention. Accordingly, depending upon whether it is ready for application or it is in concentrated form, the contemplated pesticidal compositions contain between about 0.0001 percent and about 80 percent, by weight of the compositions, of a pesticidal compound of this invention and a carrier, liquid or solid, as defined hereinbefore.

INSECTICIDE TEST METHODS

Bait Test [Housefly (adult)]

Method of Treatment

One milliliter of an aqueous solution or suspension of the candidate compound is pipetted into a 9 cm. petri dish containing filter paper and 0.1 gm. granular sugar. Ten adults are admitted and the dish is closed.

Method of Recording Results

Mortality is recorded after 24–75 hours. Compounds which product 90% mortality are reevaluated at lower concentrations in secondary tests. Mode of action may be by stomach poison, contact or vapor.

Larvicide/Growth Regulant Test (Yellow Fever Mosquito larvae)

Method of Treatment

The rearing medium is treated prior to infestation. For mosquito larvae this consists of 10 ml. of water containing 10 ppm. of the candidate compound in a plastic cup. Food is added after infesting with 5 last instar larvae. The cup is then capped.

Method of Recording Results

Mortality (larvicide) is recorded after 24 hours.

Stomach Poison—Foliar Dip Test

Primary Screen
Southern Armyworm (Larva)
Mexican Bean Beetle (Larva)

Method of Treatment

Lima bean leaves of a uniform size are momentarily dipped in a 500 ppm. water-acetone of the test material. Treated leaves are placed on moistened filter paper in 9 cm. petri dishes and allowed to air dry, and then are infested. The dishes are then closed.

Method of Recording Results

Mortality is recorded 72 hours after infestation. Compounds active at 500 ppm. are retested at 100 and 10 ppm.

Ovicide/Larvicide Test

Primary Screen
Boll Weevil (egg)

Method of Treatment

Boll Weevil - eggs are received from the USDA deposited on the surface of larval diet in 9 cm petri dishes. A segment of this egg-bearing medium, transferred to a filter paper in a clean petri dish, is treated with 2 ml. of an aqueous solution or suspension of the candidate compound, and the dish is closed.

Method of Recording Results

Observations are made for larvicidal activity through 21 days.

All test results are recorded as percent mortality. In the tabulation of data, the insect species are abbreviated as follows: Housfly (HF), Mexican Bean Bettle (MB), Southern Armyworm (SA), Yellow Fever Mosquito (YF), and Boll Weevil (BW).

The compounds of Examples 1 through 4 were subjected to the aforedescribed insecticide tests. Concentrations and results are set forth in the Table.

| Compound | Rate (PPM) | HF | YF | SA | MB | BW |
|---|---|---|---|---|---|---|
| Example 1 | 500 | 0 | | 100 | 100 | 100 |
| | 100 | — | | 65 | 95 | — |
| | 10 | | 100 | 0 | 60 | 15 |
| | 1 | | 100 | | | |
| | 0.1 | | 20 | | | |
| Example 2 | 500 | 40 | | 100 | 100 | 90 |
| | 100 | — | | 0 | 75 | 45 |
| | 10 | | 80 | | 65 | |
| | 1 | | | | | |
| Example 3 | 500 | 100 | | 0 | 90 | 20 |
| | 100 | 0 | | | | |
| | 10 | 0 | 20 | | | |
| Example 4 | 500 | 0 | | 80 | 70 | 70 |
| | 100 | | | 0 | 70 | |
| | 10 | | 80 | | 5 | |
| | 0.1 | | 0 | | | |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. Compounds having the formula:

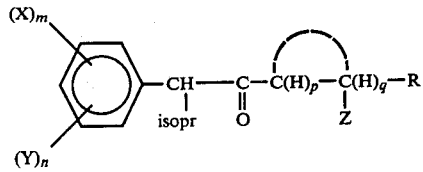

wherein isopr is isopropyl; X and Y are halogen, cyano, nitro, $C_1$-$C_4$ alkyl, $C_1$-$C_4$ alkenyl, propargyl, $C_1$-$C_4$ alkoxy, phenoxy, $C_1$-$C_4$ haloalkyl, $C_1$-$C_4$ alkylthio, or $C_1$-$C_4$ alkylsulfonyl or X and Y combined are methylenedioxy; m is 1-5; n is 0-5; m+n is not more than 5; p is 1 or 2 and q is 0 or 1 and when p is 1 and q is 0, the symbol ⌒ is a bond forming part of a double bond or a methylene group forming a cyclopropyl ring; Z is hydrogen or cyano and R is

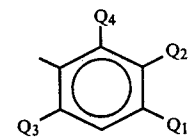

wherein $Q_2$ is phenyl, phenoxy, benzyl, propargyl, thiophenoxy, furfuryl, halogen, alkyl, hydrogen, oxothiophenyl, or trifluoromethyl; $Q_1$ is hydrogen, chlorine, phenoxy, benzyl or thiophenoxy or $Q_1$ and $Q_2$ together can be cyclopentyl or cyclohexyl; $Q_3$ is hydrogen, methyl or chlorine; and $Q_4$ is hydrogen or methyl.

2. A compound of claim 1 having the formula:

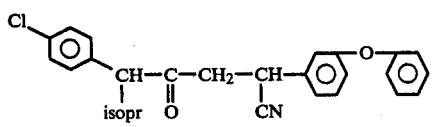

3. A compound of claim 1 having the formula:

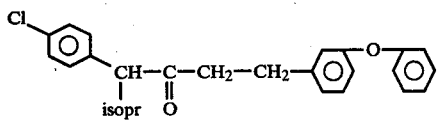

4. A compound of claim 1 having the formula:

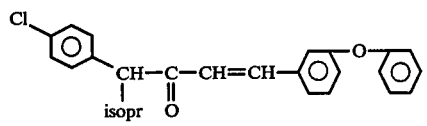

5. A compound of claim 1 having the formula:

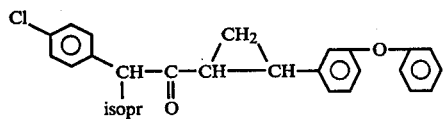

6. The method for combatting insects that comprises contacting them with an insecticidally effective amount of a compound of claim 1.

7. The method for combatting insects that comprises contacting them with an insecticidally effective amount of a compound of claim 2.

8. The method for combatting insects that comprises contacting them with an insecticidally effective amount of a compound of claim 3.

9. The method for combatting insects that comprises contacting them with an insecticidally effective amount of a compound of claim 4.

10. The method for combatting insects that comprises contacting them with an insecticidally effective amount of a compound of claim 5.

11. An insecticidal composition comprising a carrier and an insecticidally effective amount of a compound of claim 1.

12. An insecticidal composition comprising a carrier and an insecticidally effective amount of a compound of claim 2.

13. An insecticidal composition comprising a carrier and an insecticidally effective amount of a compound of claim 3.

14. An insecticidal composition comprising a carrier and an insecticidally effective amount of a compound of claim 4.

15. An insecticidal composition comprising a carrier and an insecticidally effective amount of a compound of claim 5.

* * * * *